United States Patent [19]

Matsuda

[11] 4,153,795

[45] May 8, 1979

[54] COBALT PYRIDYL CATALYSTS FOR HYDROFORMYLATION

[75] Inventor: Akio Matsuda, Kashiwa, Japan

[73] Assignee: Director-General of the Agency of Industrial Science and Technology, Tokyo, Japan

[21] Appl. No.: 818,253

[22] Filed: Jul. 22, 1977

[30] Foreign Application Priority Data

Jul. 26, 1976 [JP] Japan .................................. 51/88240

[51] Int. Cl.² ...................... C07F 15/06; C07C 45/10; C07D 401/12
[52] U.S. Cl. ........................................ 546/2; 546/267; 260/604 HF
[58] Field of Search .......................... 260/270 J; 546/2

[56] References Cited

U.S. PATENT DOCUMENTS 3,996,164   12/1976   Matsuda ............................ 260/270 J

*Primary Examiner*—Mark L. Berch
*Attorney, Agent, or Firm*—Sprung, Felfe, Horn, Lynch & Kramer

[57] ABSTRACT

Complex catalysts for hydroformylation which comprises (A) a cobalt carbonyl component and (B) at least one component selected from the group consisting of 3-pyridylpropionic acid esters of aliphatic polyhydric alcohols, 3-pyridylpropionic acid esters of aliphatic pyridylalcohols and dipyridyl ethers. The catalysts promote hydroformylation of olefins at low temperature and pressure and are especially easily separated and recovered.

7 Claims, No Drawings

COBALT PYRIDYL CATALYSTS FOR HYDROFORMYLATION

BACKGROUND OF THE INVENTION

The present invention relates to catalysts for hydroformylation of olefins and to cobalt carbonyl complexes which possess a character capable of forming aldehydes selectively at low temperature and pressure and are easily separated and recovered after the reaction and recycled for repeated uses.

Chiefly used as catalysts known to date for use in hydroformylation (oxo reaction) of olefins are cobalt carbonyl, rhodium carbonyl and derivatives thereof. As hydroformylation is a reaction which is carried out in a liquid phase having the catalyst uniformly dispersed therein, separation of the catalyst from the reaction product is necessary after the reaction. In particular, when the hydroformylation is carried out by using a catalyst of cobalt carbonyl series, the separation of cobalt carbonyl from the product after the reaction has been a very important problem from the industrial point of view. In connection with the above, therefore, a number of patents such, for example, as U.S. Pat. Nos. 3,636,159 and 3,652,676 have been issued to date. However, the majority of the prior art methods for separating cobalt carbonyl is carried out by heating the product whereby cobalt carbonyl is thermally decomposed to precipitate metallic cobalt or by treating the product with an organic or inorganic acid to convert cobalt carbonyl into an oil-soluble, water-soluble or water-insoluble cobalt salt and subsequently separating the cobalt salt in an appropriate manner depending on the behavior of the cobalt salt. The metallic cobalt or cobalt salt separated by these methods is converted again to cobalt carbonyl in a separated step of the process and repeatedly used as catalyst for the oxo reaction. Otherwise, the metalic cobalt or cobalt salt may be recycled as such to the reaction system. In this case, a relatively severe condition (for example, 150°–200° C., 200–300 atm) is required since the oxo reaction would be ceased unless a condition which permits regeneration of cobalt carbonyl from the metallic cobalt or cobalt salt be selected in the oxo reaction vessel. Another method for the recovery of cobalt carbonyl comprises converting cobalt carbonyl into water-soluble $NaCo(CO)_4$ by using $Na_2CO_3$, separating the conversion product in the form of an aqueous solution and having the separated aqueous solution reacted upon by sulfuric acid to generate $HCo(CO)_4$ which is then recycled as catalyst for the oxo reaction. In recent years, a method for separating cobalt carbonyl wherein the product is treated with a high molecular coordinating agent to convert the cobalt carbonyl into an insoluble solid which is then separated from the system has been taken up as a subject of study. However, all of the prior art methods described above inevitably require special steps for the recovery of the catalyst.

It is also known that a complex of cobalt carbonyl comprising a substituted pyridine with an electronegative non-hydrocarbon is a good catalyst for the oxo reaction (see U.S. Pat. No. 3,231,621). However, removal of the catalyst in this case requires a special measure.

The present inventor already proposed a complex of cobalt carbonyl and a pyridine compound as a catalyst for the oxo reaction (U.S. Pat. No. 3,996,164). However, this prior art required such a condition that the complex is previously prepared and then added to the reaction system. As a result of extensive researches made to overcome the drawbacks of these prior art catalysts and to improve separation characteristics and selectivity to aldehydes at low temperature and pressure, the present invention has been accomplished.

BRIEF SUMMARY OF THE INVENTION

In accordance with the present invention, there is provided a complex catalyst for hydroformylation which comprises (A) a cobalt carbonyl component and (B) a component comprising a compound having at least two pyridyl groups in the molecule.

It is an object of the present invention to provide a complex of cobalt carbonyl series which is suitable for hydroformylation of olefin and capable of producing aldehydes at a high selectivity at low temperature and pressure.

It is another object of the present invention to provide a complex of cobalt carbonyl series which is easily separated and recovered after completion of the reaction and is easily recycled for repeated uses.

It is further object of the present invention to provide a process for carrying out hydroformylation of olefins suitably wherein a new complex of cobalt carbonyl series is used.

It is still another object of the present invention to provide a process for the preparation of a new complex of cobalt carbonyl series.

Other and further objects, features and advantages of the present invention will appear more fully from the following description.

DETAILED DESCRIPTION OF THE INVENTION

Examples of the cobalt carbonyl component (A) utilizable for the preparation of the complex catalyst of the present invention include cobalt carbonyl itself represented by the formula $[Co_2(CO)_8]$ and cobalt compounds capable of forming cobalt carbonyl under the reaction condition for hydroformylation, such as cobalt carbonate, cobalt naphthenate and metallic cobalt.

The component (B) having at least two pyridyl groups in its molecule, which is utilisable as ligand in the complex catalyst of the present invention is selected from (I) 3-pyridylpropionic acid esters of aliphatic polyhydric alcohols, (II) 3-pyridylpropionic acid esters of aliphatic pyridyl alcohol and (III) dipyridyl ethers. These compounds are represented by the following general formulas:

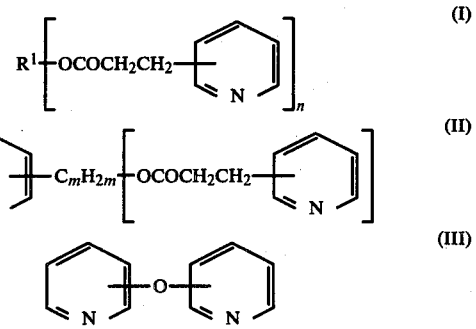

wherein $R^1$ stands for a residue of an aliphatic polyhydric alcohol, n for a valence of the residue of the aliphatic polyhydric alcohol and normally for an integer of at least 2, and m for an integer of at least one and wherein the hydrogen atom or atoms in the pyridyl group or groups may be ring substituted by a lower alkyl group or groups.

As the aliphatic polyhydric alcohol forming the residue $R^1$, various dihydric or more alcohols, generally dihydric to hexahydric alcohols come into question. Illustrative of these alcohols are, for example, alkylene glycols of the general formula $R^2+OH)_2$ wherein $R^2$ stands for an alkylene group with 2–20 carbon atoms, generally 2–10 carbon atoms, such as ethylene glycol, propylene glycol, butandiol, pentanediol, hexanediol, octanediol and decanediol, glycerol, pentaerythritol, pentitol and hexitol. Illustrative of the substituent(s) on the pyridine ring of the component (B) are, for example, hydrogen atom, methyl group, ethyl group, propyl group and hexyl group.

The above compounds (I), (II) and (III) are new. The ester compounds (I) are prepared by subjecting an alkyl 3-pyridylpropionate of the general formula:

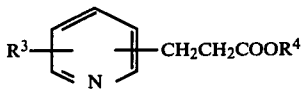

(IV)

wherein $R^3$ stands for a hydrogen atom or a lower alkyl group and $R^4$ for a lower alkyl group,
to a transesterification reaction with the above described aliphatic polyhydric alcohol of the general formula: $[R^1+OH)_n]$ wherein $R^1$ has the same meaning as given above. The reaction in this case is carried out at a temperature within the range of 150°–300° C., preferably 200°–250° C. Utilized in this case as catalyst is $NaOCH_3$. The lower alcohol formed during the transesterification reaction is continuously removed from the reaction system by distillation.

Especially preferable as the ester compound (I) are ethylene glycol, glycerol, butandiol and pentaerythritol di-, tri and tetra-[3-(2-pyridyl)-propionate].

The ester compounds (II) are prepared in a similar manner by subjecting an alkyl 3-pyridylpropionate of the above general formula (IV) to a transesterification reaction with an aliphatic pyridyl alcohol of the general formula:

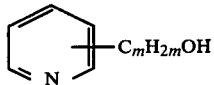

wherein m stands for the same meaning as given above.
Especially preferable as the ester compound (II) are 2-(2-pyridyl)ethyl 3-(2-pyridyl)-propionate and 3-(2-pyridyl)-propyl 3-(2-pyridyl)-propionate.

The compounds (III) are prepared by heating a hydroxypyridine of the general formula:

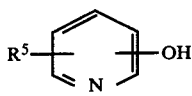

and another hydroxypyridine of the general formula:

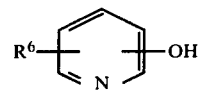

to effect dehydrocondensation reaction. In these formulas, $R^5$ and $R^6$ each represent hydrogen atom or a lower alkyl group. In this case, the reaction temperature is within the range of 150°–200° C.

Especially preferable as the ether compound (III) are di-(2-pyridyl) ether.

The proportion of the cobalt carbonyl component (A) to the component (B) in the complex catalyst of the present invention is such that the component (B) is used in an amount of 2–20 mols per mol of the component (A). If the amount of the component (B) exceeds the above value, the yield of the product will adversely be affected. On the other hand, if the amount of the component (B) is less than the above value, separation of the complex will be influenced badly. With respect to separation and yield of the complex, the most preferable result is obtained when the component (A) and the component (B) are used in such a proportion that the molar ratio of cobalt to the component (B) is within the range from 1:1 to 1:2.

The complex catalyst of the present invention is prepared by mixing the cobalt carbonyl component (A) with the ester or ether component (B) containing at least two pyridyl groups in the molecule at a temperature ranging from room temperature to 100° C. The formation of the complex may be performed in the reactor for hydroformylation.

The hydroformylation of olefins using the catalyst of the present invention is carried out by placing in a reactor the complex catalyst of the present invention or the cobalt carbonyl component (A) and the ester component (B) capable of forming the complex, an olefin and an optional solvent such as liquid paraffin or diethyl ether, and reacting the olefin with a synthetic gas (an equimolar mixture of CO and $H_2$) under pressure at a temperature of 50°–100° C. and at a pressure of 5–100 atm. After completion of the reaction, the reaction liquid is cooled at room temperature whereby the complex catalyst forms a red viscous lower layer and is separated from the almost colorless product. The separated catalyst is recovered and recycled for the next reaction. The catalyst is allowed to be present in an amount of 0.5–50 parts by weight, preferably 2–20 parts by weight per 100 parts by weight of the starting olefin.

The complex catalyst of the present invention is represented by the empirical formula: $H_2Co_3(CO)_9(B)_a$ wherein B stands for the above difined component (B) having at least 2 pyridyl groups in its molecule and a for the number of the component (B). As the component (B) has at least 2 pyridyl groups in its molecule, the number a is preferably within the range of $3 \leq n \leq 5$ wherein n stands for a positive number although the number a may theoretically be a value of 2.5 or less, but not less than 1.25.

As is evident from U.S. Pat. No. 3,996,164 wherein the present inventor proposed, as described above, a process for the preparation of a complex of cobalt carbonyl and pyridine, the complex is represented by the empirical formula: $H_2Co_3(CO)_9(Py)_5$ wherein Py stands for pyridine, and revealed that the complex has the ion pair structure of $\{Co(H^+)_2(Py)_5(CO)\}\{Co(CO)_4^-\}_2$ and shows strong absorption band at 1890 cm$^{-1}$ which is characteristic of $Co(CO)_4-$ and weak absorption band at 2010 cm$^{-1}$ which is characteristic of the cation moiety of the structure and an absorption band at 1600 cm$^{-1}$ which is characteristic of pyridyl group. The complex catalyst of the present invention likewise shows the same absorption bands in respect of $Co(CO)_4-$ and pyridyl group, thus indicating that the pyridine compound in the present invention is coordinated without any reaction as in the case of pyridine. Thus, it is firmly believed that the complex catalyst of the present invention has the above empirical formula.

Unlike the case of the prior art catalysts, no special separation step is necessary for the complex catalyst of the present invention. The complex catalyst has such advantages that it can be separated simply by cooling the reaction product after hydroformylation of olefins and that the separated catalyst can be recycled as such for the next reaction. In contrast with the case of the prior art catalysts of cobalt series used under high temperature and pressure conditions such as a reaction temperature of 150°–200° C. and a reaction pressure of 200–300 atm, the complex catalyst of the present invention is used under very mild conditions including a reaction temperature of 50°–100° C., a total pressure of 10–50 atm and a partial pressure of carbon monoxide of 0.1–20 atm. Thus, the complex catalyst of the present invention is advantageous in that hydrogen containing only 10% or less of carbon monoxide can be used as starting gas and that aldehydes can be produced at a high selectively and simultaneously the carbon monoxide contained in the hydrogen gas can almost entirely be removed. Thus, the complex catalyst of the present invention is of great industrial significance, particularly in that the complex catalyst makes it possible to synthetize aldehydes at a high selectivity even at low temperature and pressure and simultaneously to effect the purification of the hydrogen used.

The present invention will be more clearly understood with reference to the following examples.

EXAMPLE 1

Preparation of alkyl 3-(2-pyridyl)-propionates

An about 300 ml vertical agitation type stainless steel autoclave was charged with 0.5 mol of 2-vinylpyridine, 0.5 mol of methanol, 1 g of $Co_2(CO)_8$ and 100 ml of benzene as solvent. The mixture was reacted under pressure of carbon monoxide at 170° C. and 100 atm for 5 hours. The resultant product was distilled whereby 47.8 g of a fraction distilled at 118° C./10 mm Hg were obtained.

This fraction showed an absorption band of ester at 1730 cm$^{-1}$ in IR-absorption spectroanalysis and was identified to be methyl 3-(2-pyridyl)-propionate from the result of NMR absorption spectroanalysis.

In a similar manner, an autoclave was charged with 0.25 mol of 2-vinylpyridine, 1 mol of ethanol, 1 g of $Co_2(CO)_8$ and 100 ml of benzene as solvent and the mixture was reacted under pressure of carbon monoxide at 170° C. and 70 atm for 2 hours. The resultant product was distilled whereby 32.0 g of a fraction distilled at 122° C./10 mm Hg were obtained. This fraction was identified to be ethyl 3-(2-pyridyl)-propionate from the results of IR-absorption and NMR-absorption spectroanalyses.

EXAMPLE 2

Preparation of ethylene glycol 3-(2-pyridyl)-propionate

A transesterification reaction was carried out by placing 0.05 mol of ethylene glycol and 0.17 mol of methyl 3-(2-pyridyl) propionate in a flask equipped with a fractionating column and stirring the mixture for 40 hours at 200° C. During this treatment, 3.4 cc of methanol was distilled off.

The resultant product was distilled whereby 14.0 g of a fraction distilled at 200°–210° C./1 mm Hg were obtained, which showed an absorption band of ester at 1730 cm$^{-1}$ but no absorption band of hydroxyl group at 3200 cm$^{-1}$ and hence was identified to be ethylene glycol di-[3-(2-pyridyl) propionate].

EXAMPLE 3

Preparation of various esters of polyhydric alcohols

Transesterification reactions were carried out in the same manner as described in Example 2 except that various polyhydric alcohols were used in place of ethylene glycol to obtain corresponding esters. The boiling points of the obtained esters at 1 mm Hg and the type of the polyhydric alcohols used are shown in Table 1.

Table 1

| Exp. No. | Polyhydric alcohol | Boiling point of the obtained ester (1mmHg) |
|---|---|---|
| 1 | 1,4-butandiol | 220°–230° C. |
| 2 | glycerine | 210°–223° C. |
| 3 | pentaerythritol | 250°–260° C. |

EXAMPLE 4

Preparation of 2-(2-pyridyl) ethyl 3-(2-pyridyl)-propionate

Nine grams of ehyl 3-(2-pyridyl) propionate and 5.7 g of 2-(2-pyridyl) ethanol were reacted for 2 hours at 200° C. in the presence of 0.01 g of sodium methylate. By distillation of the product in vacuo, 4 g of a fraction which distilled at 140°–145° C. at 0.5 mm Hg were obtained.

The fraction exhibited an absorption band of ester at 1710–1730 cm$^{-1}$ in IR-absorption spectroanalysis and was identified to be 2-(2-pyridyl) ethyl 3-(2-pyridyl)-propionate.

EXAMPLE 5

Preparation of di(pyridyl) ether

A stainless steel vertical agitation type autoclave was charged with 0.25 mol of 2-hydroxypyridine and 100 ml of benzene as solvent and the mixture was reacted at 170° C. for 3 hours. The product was distilled whereby 18.8 g of a fraction distilled at 135° C./0.2 mm Hg were obtained. This fraction showed an absorption band of ether at 1240 cm$^{-1}$ in IR-absorption spectroanalysis and was identified to be di(pyridyl) ether from the result of NMR absorption spectroanalysis.

EXAMPLE 6

An about 400 ml vertical agitation type stainless steel autoclave was charged with 0.2 mols of the starting 1-decene, 30 g of liquid paraffin as solvent and 8 m-mols of $Co_2(CO)_8$ and 20 m-mols of ethylene glycol di-[3-(2-pyridyl)-propionate] as catalyst components. After pressurizing the autoclave with the synthetic gas (a 1:1 mixture of carbon monoxide and hydrogen), the mixture was heated at 80° C. and 500 atm, while supplying the synthetic gas from a pressure reservoir, and reacted for 4 hours while maintaining the above described temperature and pressure. After completion of the reaction, the autoclave was cooled to room temperature whereby 98.9% of the cobalt carbonyl was coordinated with the ester to form a red viscous complex which was separated from the liquid paraffin phase containing the product. A study of IR-absorption spectrograph of this complex revealed a strong absorption band at 1890 cm$^{-1}$ characteristic of Co(CO)$_4-$, a weak absorption band at 2010 cm$^{-1}$ and an absorption band at 1600 cm$^{-1}$ characteristic of pyridyl group. The pattern of this IR-absorption spectrograph is quite identical with that of the pyridine complex H$_2$Co$_3$(CO)$_9$(Py)$_5$, indicating similarity of the complex of the present invention to the above described pyridine complex. An elementary analysis of the complex thus obtained gave the following result:

| Co | C | H | N | O |
|---|---|---|---|---|
| 10.7% | 55.3% | 4.6% | 6.3% | (remainder) |

A study of the complex according to the proton NMR method revealed that an absorption band characteristic of the hydride proton coordinated to cobalt was found at $-0.84$ ppm.

From all of these results, it was confirmed that the complex had an empirical formula of H$_2$Co$_3$(CO)$_9$(B$_1$)$_{3.75}$ wherein B$_1$ stands for ethylene glycol di[3-(2-pyridyl)propionate], and was a mixture of H$_2$Co$_3$(CO)$_9$(B$_1$)$_4$ and H$_2$Co$_3$(CO)$_9$(B$_1$)$_3$.

In this reaction system, the conversion rate of the 1-decene was 87.2% and the production rate of aldehydes was as follows: 64.6% straight chain undecanal, 27.2% α-methyldecanal and 8.2% other branched chain aldehydes.

EXAMPLE 7

An autoclave containing the complex separated in Example 6 was charged with 0.2 mol of 1-decene and 30 g of liquid paraffin and the mixture was reacted at 80° C. and 20 atm for 4 hours according to the same operation as described in Example 6.

After the completion of the reaction, the autoclave was cooled to room temperature whereby 98.7% of the cobalt carbonyl was converted into a red viscous complex which was separated from the liquid paraffin phase containing the product. As a result of the reaction, the conversion rate of the 1-decene was 72.7% and the production rate of aldehydes were as follows: 48.0% straight chain undercanal, 37.4% α-methyldecanal and 14.6% other branched chain aldehydes.

EXAMPLE 8

The reaction of Example 6 was repeated except that 4 m-mols of Co$_2$(CO)$_8$ and 10 m-mols of 1,4-butandiol di[3-(2-pyridyl)propionate] were used as catalyst and that the reaction was carried out for one hour at 100° C. and 50 atm. After completion of the reaction, the autoclave was cooled to room temperature whereby 98.5% of the cobalt carbonyl was converted into a red viscous ester complex which was separated from the liquid paraffin phase containing the product. As a result of the reaction, the conversion rate of the 1-decene was 77.1% and the production rate of aldehydes was as follows: 52.8% straight chain undercanal, 33.4% α-methyldecanal and 13.8% other branched chain aldehydes.

A study of the IR-absorption spectrograph of the complex obtained in this manner revealed that his complex showed the absorption bands of Co(CO)$_4-$ and the pyridyl group as in the case of Example 6. As a result of investigation on the structure of this complex by way of elementary analysis and NMR method performed in the same manner as described in Example 6, it was confirmed that the complex had an empirical formula- H$_2$Co$_3$(CO)$_9$(B$_2$)$_{3.75}$ wherein B$_2$ stands for 1,4-butandiol di-[3-(2-pyridyl)-propionate].

EXAMPLE 9

An autoclave containing the complex separated in Example 8 was charged with 0.2 mol of 1-decene and 30 g of liquid paraffin and the mixture was reacted at 100° C. and 50 atm for one hour according to the same operation as described in Example 8. After the reaction, the autoclave was cooled to room temperature whereby 97.9% of the cobalt carbonyl was converted into a red viscous complex which was separated from the liquid paraffin phase containing the product. As a result of the reaction, the conversion rate of the 1-decene was 87.2% and the production rate of aldehydes was as follows: 55.0% straight chain undecanal, 33.8% α-methyldecanal and 11.2% other branched chain aldehydes.

EXAMPLE 10

The reaction was carried out in the same manner as described in Example 8 except that 4 m-mols of Co$_2$(CO)$_8$ and 10 m-mols of pentaerythritol tetra [3-(2-pyridyl)-propionate] were used as catalyst. After the reaction, the autoclave was cooled to room temperature whereby 97.3% of the cobalt carbonyl was converted into a red viscous complex with the ester, which was separated from the liquid paraffin phase containing the product. The conversion rate of the 1-decene was 83.5% and the production rate of aldehydes was as follows: 57.2% straight chain undecanal, 26.7% α-methyldecanal and 16.0% other branched chain aldehydes. Analysis of the complex thus obtained was performed in the same manner as described in Example 6 whereby the complex was found to have an empirical formula: H$_2$Co$_3$(CO)$_9$(B$_3$)$_{3.75}$ wherein B$_3$ stands for pentaerythritol tetra [3-(2-pyridyl)-propionate].

EXAMPLE 11

An about 300 ml vertical agitation type stainless steel autoclave was charged with 0.1 mol of 1-decene, 30 g of diethyl ether as solvent and 4 m-mols of Co$_2$(CO)$_8$ and 0.7 m-mols of ethylene glycol di[3-(2-pyridyl)-propionate]. After pressurizing the autoclave with hydrogen containing 3.8% carbon monoxide up to 100 atm, the mixture was heated at 60° C. and reacted under agitation for 5 hours at a definite temperature. After the reaction, the gaseous phase contained only 0.06% of carbon monoxide so that the hydrogen was recovered as having a purity as high as 99.94%. 99.3 percents of the complex were separated as a dark red viscous liquid from the product phase. Analysis of the complex thus obtained was performed in the same manner as discribed in Example 6 whereby the comlex was found to have an empirical formula H$_2$Co$_3$(CO)$_9$(B$_1$)$_4$ wherein B$_1$ has the same meaning as given above.

From the starting 1-decene, aldehydes in an equimolar amount (0.0375 mol) to the consumed carbon monoxide were produced. The production rate of the aldehydes was as follows: 62.2% of straight chain undecanal, 23.0% α-methyldecanal and 14.8% other branched chain aldehydes.

EXAMPLE 12

The same autoclave as described in Example 6 was charged with 0.2 mol of the starting 1-decene, 30 g liquid paraffin as solvent and 1 m-mol of $Co_2(CO)_8$ and 2.67 m-mols of 2-(2-pyridyl)-ethyl 3-(2-pyridyl)-propionate as catalyst. After pressurizing the autoclave with the synthetic gas, the mixture was heated at 100° C. and 50 atm, while supplying the synthetic gas from a pressure reservoir, and reacted for one hour under agitation while maintaining the temperature and pressure. After completion of the reaction, the autoclave was cooled to room temperature whereby 80% of the cobalt carbonyl was converted into a red viscous complex which was separated from the liquid paraffin phase. The conversion rate of the 1-decene was 77.6% while the production rate of aldehydes was as follows: 58.4% straight chain undecanal, 25.8% α-methyldecanal and 15.8% other branched chain aldehydes.

The complex thus obtained was found to have an empirical formula: $H_2Co_3(CO)_9(B_4)_4$ wherein $B_4$ stands for 2-(2-pyridyl)-ethyl 3-(2-pyridyl)-propionate.

EXAMPLE 13

An about 400 ml vertical agitation type stainless steel autoclave was charged with 0.2 mol of 1-decene, 30 g of liquid paraffin as solvent and 4 m-mols of $Co_2(CO)_8$ and 10 m-mols of the above mentioned di(2-pyridyl) ether as catalyst. The mixture was heated under pressure of the synthetic gas (a 1:1 gaseous mixture of carbon monoxide and hydrogen) at 100° C. and 50 atm, while supplying the synthetic gas from a pressure reservoir and reacted under agitation for 4.5 hours while maintaining the pressure constantly. After completion of the reaction, the autoclave was cooled to room temperature whereby 98.0% of cobalt carbonyl was converted into a red viscous complex which was separated as the lowere layer from the liquid paraffin layer containing the product. The conversion rate of the 1-decene was 82.8% while the procution rate of aldehydes was as follows: 50.9% straight chain undecanal, 34.8% α-methyldecanal and 14.3% other branched chain aldehydes. The complex thus obtained was found to have the following empirical formula: $H_2Co_3(CO)_9(B_5)_{3.75}$ wherein $B_5$ stands for di(2-pyridyl) ether.

EXAMPLE 14

The same autoclave as used in Example 6 was charged with 8 m-mol of $Co_2(CO)_8$, 20 m-mol of ethylene glycol bis-[3-(2-pyridyl)-propionate] and 30 g of benzene as solvent and then pressurized with the synthetic gas. The mixture was heated at 80° C. and 50 atm for 2 hours under agitation. The autoclave was then cooled to room temperature whereby a red viscous complex was separated from the benzene solvent. Since neither cobalt component nor ester component was detected in the benzene solvent, the composition of the separated complex was believed to correspond to $H_2Co_3(CO)_9(B)_{3.75}$ wherein B stands for the ester component. The benzene solvent was drained off and the autoclave containing the complex was then charged with 0.2 mol of 1-decene and 30 g of diethyl ether as solvent. After pressurizing the autoclave with the synthetic gas, the mixture was heated at 70° C. and 50 atm, while supplying the synthetic gas from a pressure reservoir, and reacted for 4 hours while maintaing the above described temperature and pressure. After completion of the reaction, the autoclave was cooled to room temperature whereby 98.0% of the complex was separated from the solvent phase containing the product and deposited on the bottom of the autoclave. The conversion rate of the 1-decene was 58%. The production rate of various aldehydes was as follows: 71.9% straight-chain undecanal, 19.1% α-methyldecanal and 9.0% other branched chain aldehydes.

What is claimed is:

1. A complex catalyst for hydroformylation which is a complex formed by mixing (A) with (B) an ester compound or ether compound having at least two pyridyl groups in the molecule thereof and selected from the group consisting of compounds of the formulas:

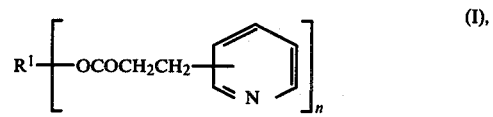
(I),

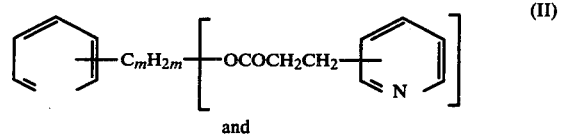
(II)

and

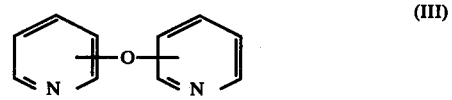
(III)

wherein $R^1$ stands for a residue of an aliphatic polyhydric alcohol with 2–20 carbon atoms, n for a valence of said residue of said aliphatic polyhydric alcohol and for an integer of at least 2 and m for an integer of at least one and wherein the hydrogen atom or atoms in the pyridyl ring or rings may be displaced by a lower alkyl group or groups.

2. A complex catalyst according to claim 1 wherein said residue $R^1$ in said component (B) is an alkylene group with 2–20 carbon atoms.

3. A complex catalyst according to claim 1 wherein said valence n in said component (B) is 2–6.

4. A complex catalyst according to claim 1 wherein the hydrogen atom or atoms in said pyridyl ring or rings are displaced by an alkyl group or groups with 1–6 carbon atoms.

5. A complex catalyst according to claim 1 wherein (B) is at least one compound selected from the group consisting of esters of ethylene glycol, glycerol, 1,4-butandiol and pentaerythritol with 3-(2-pyridyl)-propionic acid; 2-(2-pyridyl)-ethyl 3-(2-pyridyl)-propionate, 3-(2-pyridyl)-propyl 3-(2-pyridyl)-propionate; and di(2-pyridyl) ether.

6. A complex catalyst according to claim 1 wherein one molar proportion of said component (A) is coordinated with 2–20 molar proportion of said component (B).

7. A complex of the formula:

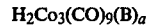

wherein B stands for a compound selected from the group consisting of esters of ethylene glycol, glycerol, 1,4-butandiol and pentaerythritol with 3-(2-pyridyl)-propionic acid; 2-(2-pyridyl)-ethyl 3-(2-pyridyl)-propionate, 3-(2pyridyl)-ethyl 3-(2-pyridyl)-propionates; and di-(2-pyridyl) ether, and a for an positive number from 1.25–5.0.

* * * * *